(12) United States Patent
Brown

(10) Patent No.: US 11,067,789 B2
(45) Date of Patent: Jul. 20, 2021

(54) BORESCOPE WAND PROTECTION SYSTEM

(71) Applicant: General Electric Company, Schenectady, NY (US)

(72) Inventor: Bruce Vincent Brown, Greenville, SC (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1035 days.

(21) Appl. No.: 15/237,749

(22) Filed: Aug. 16, 2016

(65) Prior Publication Data

US 2018/0052318 A1  Feb. 22, 2018

(51) Int. Cl.
 *G02B 23/24* (2006.01)
 *A61B 1/00* (2006.01)
 *A61B 1/005* (2006.01)

(52) U.S. Cl.
 CPC ...... *G02B 23/2476* (2013.01); *A61B 1/00039* (2013.01); *A61B 1/0051* (2013.01); *A61B 1/00052* (2013.01); *A61B 1/00078* (2013.01); *A61B 1/00087* (2013.01); *A61B 1/00089* (2013.01); *A61B 1/00101* (2013.01)

(58) Field of Classification Search
 CPC ............ G02B 23/2476; A61B 1/00039; A61B 1/00052; A61B 1/00078; A61B 1/00087; A61B 1/00089; A61B 1/00101; A61B 1/0051

USPC .............................. 359/808; 356/241.1–246.1
See application file for complete search history.

(56) References Cited

U.S. PATENT DOCUMENTS

| | | | | |
|---|---|---|---|---|
| 3,434,775 A | * | 3/1969 | Gosselin | G02B 23/26 174/115 |
| 4,319,563 A | * | 3/1982 | Kubota | A61B 1/00096 600/129 |
| 2006/0167340 A1 | * | 7/2006 | Pease | A61B 1/00052 600/127 |

* cited by examiner

*Primary Examiner* — Marin Pichler
*Assistant Examiner* — Mitchell T Oestreich
(74) *Attorney, Agent, or Firm* — Dority & Manning, P.A.

(57) ABSTRACT

The present disclosure is directed to a borescope. The borescope includes a borescope wand having a base portion, an articulating portion, a lens end, and an outer surface. A lens is positioned in the lens end of the borescope wand. A sleeve is positioned around a portion of the outer surface of the borescope wand. The sleeve is spaced apart from the lens. An end cap defines a passage extending therethrough from a first opening to a second opening. The lens end of the borescope wand extends through the first opening and is positioned within the passage such that the lens is positioned between the first opening and the second opening.

18 Claims, 5 Drawing Sheets

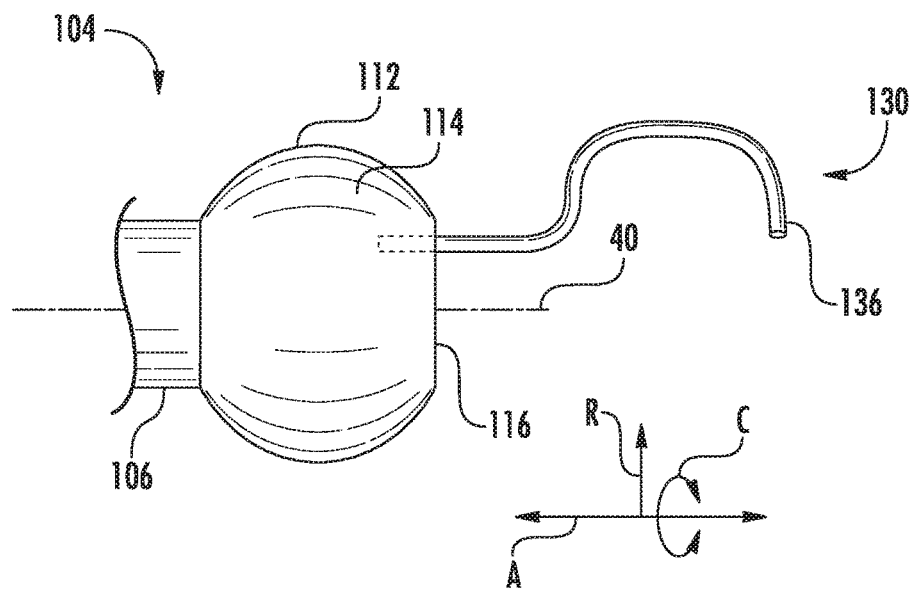
FIG. 8
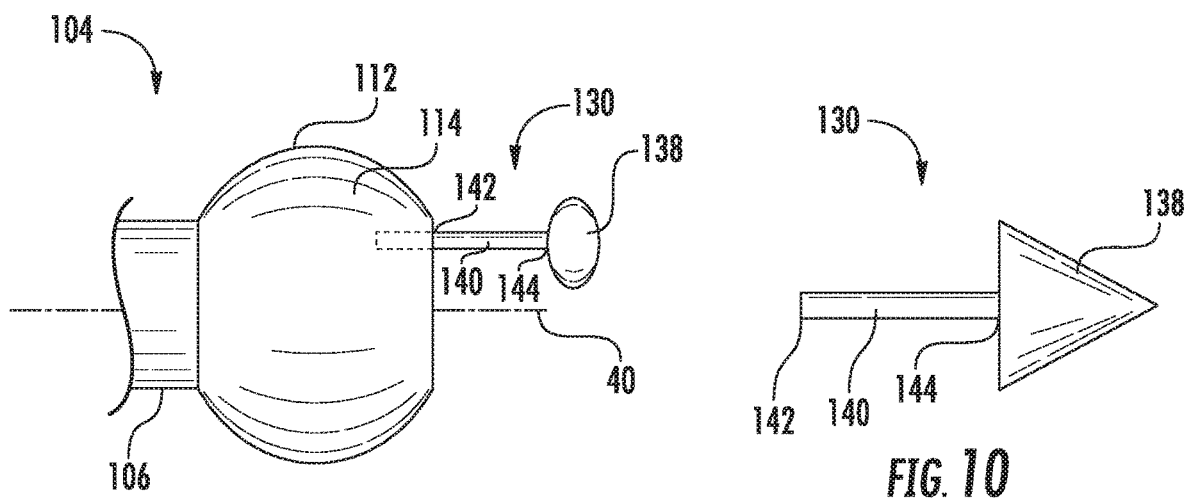
FIG. 9
FIG. 10

BORESCOPE WAND PROTECTION SYSTEM

FIELD OF THE TECHNOLOGY

The present disclosure generally relates to borescopes. More particularly, the present disclosure relates to wand protection systems for borescopes.

BACKGROUND

Borescopes are instruments that may be used to inspect or otherwise view objects that are normally inaccessible to visual inspection. In this respect, borescopes typically include a flexible borescope wand having a lens positioned therein. The borescope wand may fit into small spaces and other areas inaccessible to the human eye. The flexible nature of the borescope wand also permits viewing of objects located in places where a direct line of sight is not available, such an object positioned in a curved passage.

Borescopes are commonly used to inspect various components and features in gas turbine engines. Specifically, the borescope wand may fit into various cavities and passages in the gas turbine engine to permit viewing of normally inaccessible features. In this respect, the borescope wand may have to slide through various passages and compartments to place the lens in a position to view the desired feature. During this sliding, the lens and portions of the borescope wand may contact various components (walls, edges, etc.) in the gas turbine. This contact causes wear to the borescope wand, thereby reducing the service life of the borescope. Specifically, the borescope wand experiences wear on an articulating portion thereof. This wear also increases the number of maintenance intervals necessary during the service life of the borescope. Furthermore, contact between the lens and the various gas turbine components may scratch or otherwise damage the lens.

Accordingly improved borescopes are desired. In particular, borescopes with components to reduce wear on the borescope wand would be advantageous.

BRIEF DESCRIPTION OF THE TECHNOLOGY

Aspects and advantages of the technology will be set forth in part in the following description, or may be obvious from the description, or may be learned through practice of the technology.

In one aspect, the present disclosure is directed to a borescope having a borescope wand. The borescope wand includes an outer surface having a base portion, an articulating portion, and a lens end. A lens is positioned in the lens end of the borescope wand. A sleeve is positioned around a portion of the outer surface of the borescope wand. The sleeve is spaced apart from the lens. An end cap defines a passage extending therethrough from a first opening to a second opening. The lens end of the borescope wand extends through the first opening and is positioned within the passage such that the lens is positioned between the first opening and the second opening.

In a further aspect, the present disclosure is directed to a borescope having a borescope wand. The borescope wand includes a base portion having a base portion outer surface, an articulating portion having an articulating portion outer surface, and a lens end having a lens end outer surface. A lens is positioned in the lens end of the borescope wand. A helical spring is positioned around the articulating portion outer surface of the borescope wand. The helical spring is spaced apart from the lens. An end cap defines a passage extending therethrough from a first opening to a second opening. The lens end of the borescope wand extends through the first opening and is positioned within the passage such that the lens is positioned between the first opening and the second opening.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended FIGS., in which:

FIG. 8 is a side view of the end cap, illustrating one embodiment of an auxiliary attachment extending outwardly therefrom according to embodiments of the present disclosure;

FIG. 9 is a side view of the end cap, illustrating another embodiment of the auxiliary attachment extending outwardly therefrom according to embodiments of the present disclosure; and FIG. 10 is a side view of a further embodiment of the auxiliary attachment according to embodiments of the present disclosure.

Figure 1:
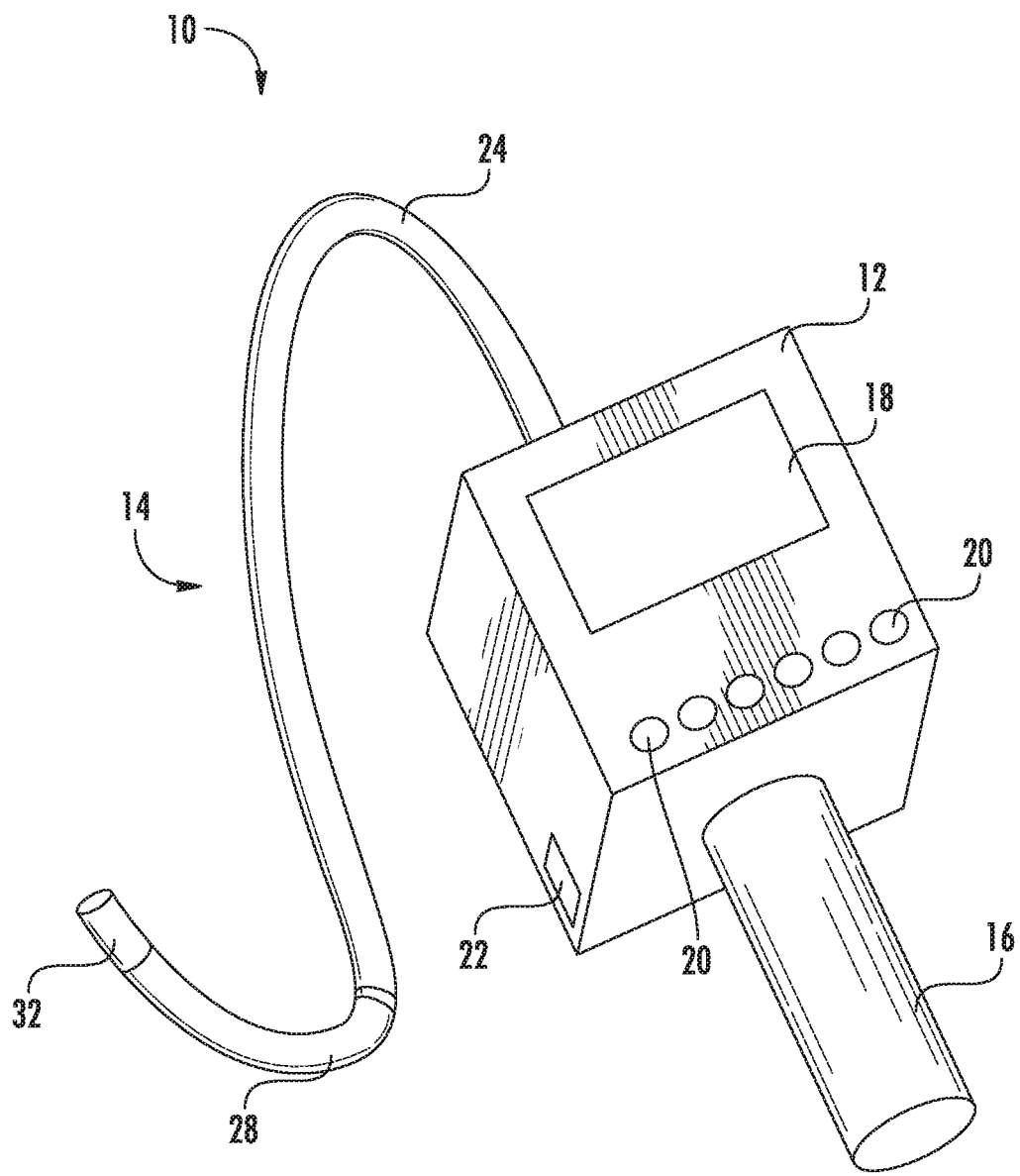
FIG. 1 is a perspective view of an exemplary borescope, which includes a borescope wand, according to embodiments of the present disclosure.

Repeat use of reference characters in the present specification and drawings is intended to represent the same or analogous features or elements of the present technology.

DETAILED DESCRIPTION OF THE TECHNOLOGY

Reference will now be made in detail to present embodiments of the technology, one or more examples of which are illustrated in the accompanying drawings. The detailed description uses numerical and letter designations to refer to features in the drawings. Like or similar designations in the drawings and description have been used to refer to like or similar parts of the technology. As used herein, the terms "first", "second", and "third" may be used interchangeably to distinguish one component from another and are not intended to signify location or importance of the individual components.

Each example is provided by way of explanation of the technology, not limitation of the technology. In fact, it will be apparent to those skilled in the art that modifications and variations can be made in the present technology without departing from the scope or spirit thereof. For instance, features illustrated or described as part of one embodiment may be used on another embodiment to yield a still further embodiment. Thus, it is intended that the present technology covers such modifications and variations as come within the scope of the appended claims and their equivalents.

Now referring to the drawings, wherein identical numerals indicate the same elements throughout the figures, FIG. 1 schematically illustrates an exemplary borescope 10. As depicted therein, the borescope 10 may include a body portion 12, a borescope wand 14, and a handle 16. In the embodiment shown in FIG. 1, the borescope wand 14 and the handle 16 extend outwardly from different sides of the body portion 12. Alternatively, the borescope wand 14 and the handle 16 may extend outwardly from the same side of the body portion 12.

FIG. 1 illustrates one embodiment of the body portion 12. More specifically, the body portion 12 may include a screen 18 for viewing an image captured by the borescope. One or more controls 20 (e.g., dials, buttons, switches, etc.) may permit adjustment of various settings of the borescope 10. Some embodiments of the body portion 12 may include one or more communication ports 22 (e.g., USB ports, etc.) to permit communication and/or data exchange between the borescope 10 and, e.g., an external computer (not shown). The body portion 12 may include additional components (e.g., various electronics, etc.) as well.

Figure 2:
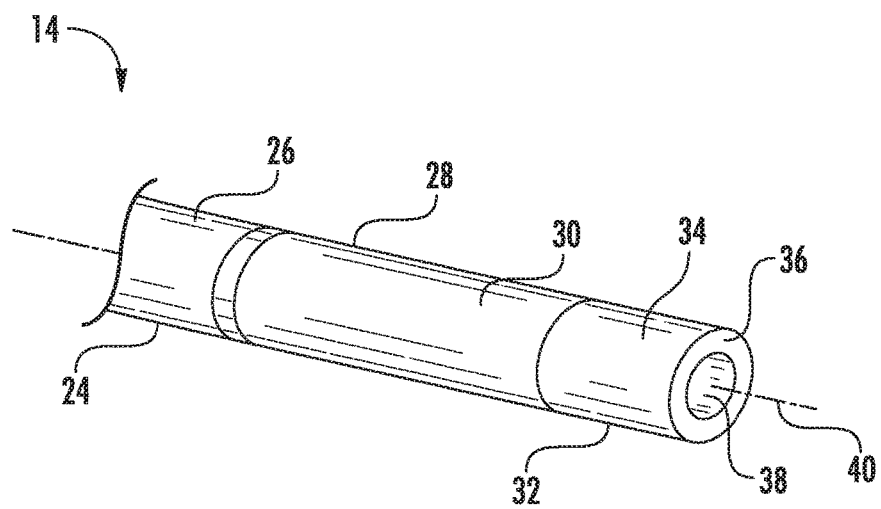
FIG. 2 is a perspective view of a portion of the borescope wand shown in FIG. 1 according to embodiments of the present disclosure.

As mentioned above, the borescope wand 14 extends outward from the body portion 12. Referring now to FIGS. 1 and 2, the borescope wand 14 includes a base portion 24 having a base portion outer surface 26, an articulating portion 28 having an articulating portion outer surface 30, and a lens end 32 having a lens end outer surface 34. The base portion outer surface 26, the articulating portion outer surface 30, and the lens end outer surface 34 generally form an outer surface of the borescope wand 14. The base portion 24 of the borescope wand 14 couples to the body portion 12 of the borescope 10 and is generally flexible (e.g., formed from a braided material). The articulating portion 28 couples to the base portion 24. In some embodiments, for example, the articulating portion 28 may include a plurality of rigid segments (not shown) pivotably coupled together in some embodiments. Alternatively, the articulating portion 28 may have other constructions. The lens end 28 couples to the articulating portion 28 and extends from the articulating portion 28 to a side surface 36 of the borescope wand 14. The lens end 32 may be rigid (e.g., formed from a metallic material) and house a lens 38.

In operation, the borescope wand 14 transmits an image from the lens 38 to the body portion 12 for viewing, e.g., on the screen 18. The flexible nature of the base portion 24 allows the borescope wand 14 to extend into or through various passages and around corners or other curves. The articulating portion 28 may be used to adjust the position of the lens 38 once the base portion 24 is in place. More specifically, articulating portion 28 may move, bend, or otherwise change position, e.g., in response to user input to the one or more controls 20 or an automated program or operation. In some embodiments, the plurality of rigid segments may pivot relative to one another. Alternatively, the articulating portion 28 may use any suitable structure to articulate. The movement of the articulated portion 28 causes movement of the lens end 32 and the lens 38. In this respect, the articulating portion 28 permits adjustment of the lens 38.

FIGS. 3-7 illustrate a borescope wand protection system 100, which may be incorporated into the borescope 10 to protect the borescope wand 14 and the lens 38. As shown in FIG. 2, the borescope wand 14 defines a longitudinal axis 40 extending therethrough. In this respect, the borescope wand protection system 100 defines an axial direction A, a radial direction R, and a circumferential direction C. In general, the axial direction A extends parallel to the longitudinal axis 40, the radial direction R extends orthogonally outward from the longitudinal axis 40, and the circumferential direction C extends concentrically around the longitudinal axis 40.

Figure 3:
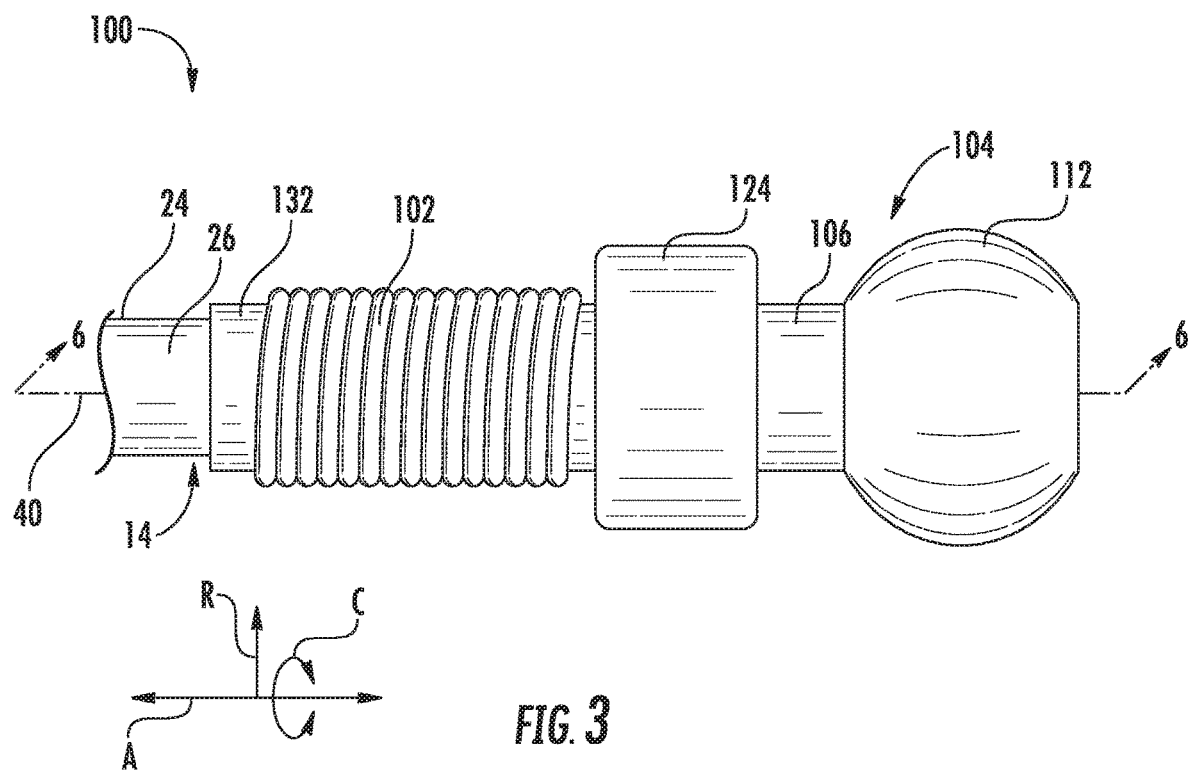
FIG. 3 is a side view of a borescope wand protection system, which includes a sleeve and an end cap, coupled to the borescope wand according to embodiments of the present disclosure.

FIG. 3 shows one embodiment of the borescope wand protection system 100 installed onto the borescope wand 14. As depicted therein, the borescope wand protection system 100 includes a sleeve 102 positioned around the articulating portion outer surface 30 of the borescope wand 14. As such, the sleeve 102 is axially spaced apart from the lens 38. The sleeve 102 protects the articulating portion 28 from wear or damage resulting from contact with, e.g., various gas turbine components (not shown). In this respect, the sleeve 102 may generally have the same axial length as the articulating portion 28. Alternatively, the sleeve 102 may be longer or shorter in the axial direction A than the articulating portion 28. Furthermore, the sleeve 102 should be flexible enough to bend as the articulating portion 28 bends. In the embodiment shown in FIG. 3, the sleeve 102 is a metallic helical spring. In alternate embodiments, the sleeve 102 may formed from a braided metallic or polymeric material. Nevertheless, the sleeve 102 may have any suitable construction or be formed from any suitable material.

Figure 4:
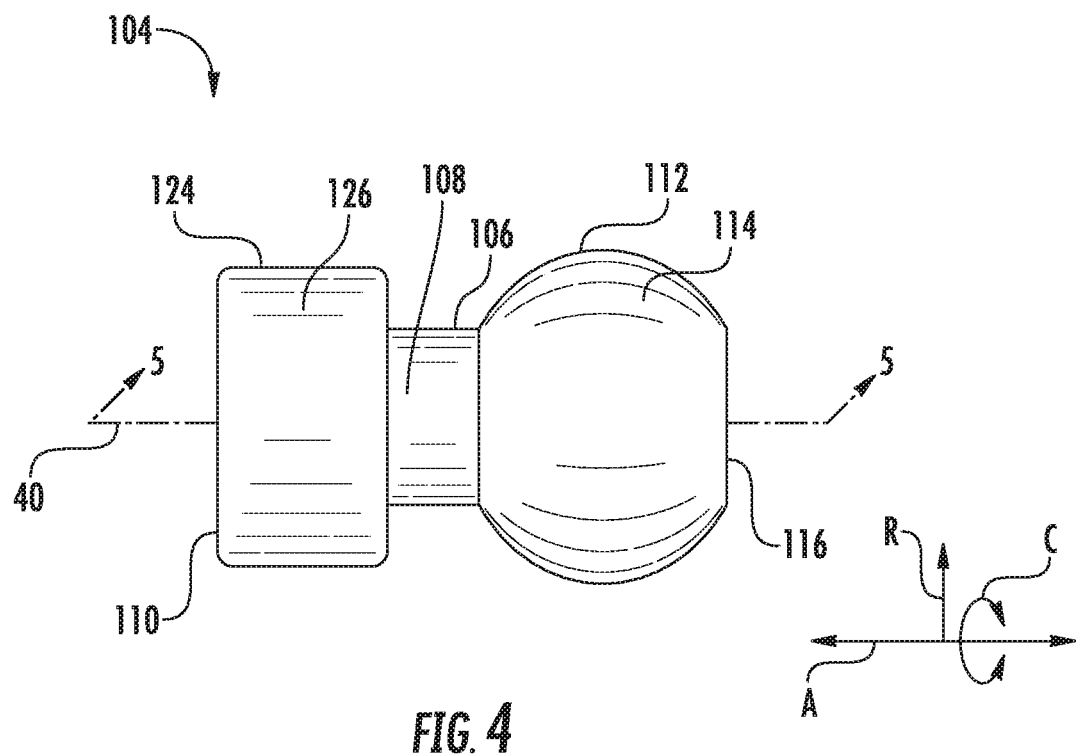
FIG. 4 is a side view of the end cap shown in FIG. 3.
Figure 5:
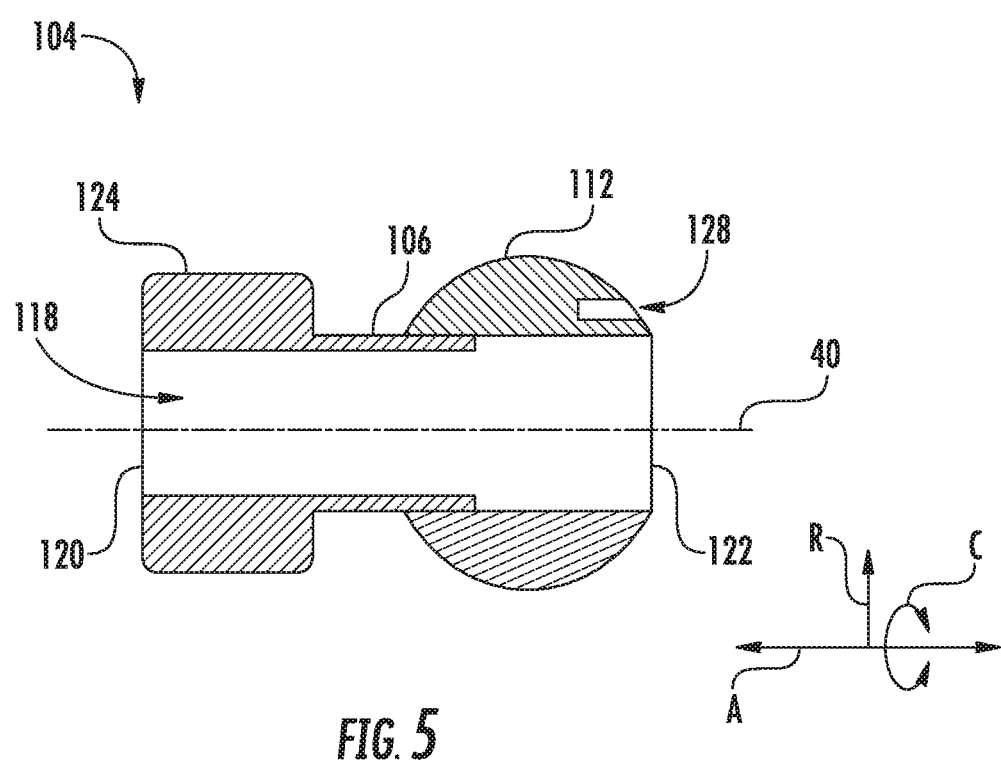
FIG. 5 is a cross-sectional view of the end cap shown in FIG. 4 taken generally about line 5-5.

The borescope wand protection system 100 also includes an end cap 104 for protecting the lens end 32 and, more specifically, the lens 38 from damage resulting from contact with, e.g., various gas turbine components (not shown). Referring now to FIGS. 3-5, the end cap 104 includes a tubular portion 106 having a tubular portion outer surface 108 and a tubular portion side surface 110. The end cap 104 also includes a spherical portion 112 having a spherical portion outer surface 114 and a spherical portion side surface 116. The spherical portion 112 may removably couple to the tubular portion 106 threadingly, via a set screw (not shown), or via any other suitable method. In other embodiments, the tubular portion 106 and the spherical portion 112 may be permanently joined (e.g., via welding, brazing, etc.) or integrally formed together. The tubular portion side surface 110 and the spherical portion side surface 116 are axially spaced apart as shown in FIG. 4 when the tubular portion 106 and the spherical portion 112 are coupled.

Referring particularly now to FIG. 5, the end cap 104 defines a passage 118 extending therethrough from a first opening 120 to a second opening 122. More specifically, the tubular portion 106 defines the first opening 120, and the spherical portion 112 defines the second opening 122. In this respect, the passage 118 extends through both the tubular portion 106 and the spherical portion 112. In the embodiment shown in FIG. 5, the first opening 120 is narrower than the second opening 122. Alternatively, the first opening 120 may be wider than or have the same diameter as the second opening 122 in other embodiments. As will be discussed in greater detail below, the passage 118 should be sized and shaped to accommodate the lens end 32 of the borescope wand 14.

In some embodiments, the tubular portion 106 includes a flange 124 extending radially outwardly therefrom. The flange 124 includes a flange outer surface 126. As illustrated in FIGS. 3-5, the flange 124 is preferably axially spaced apart from the spherical portion 112 when the tubular portion 106 and the spherical portion 112 are coupled. As such, the flange 124 may facilitate twisting of the tubular portion 106 to threadingly couple the tubular portion 106 and the spherical portion 112. In this respect, the flange outer surface 126 may be knurled to facilitate gripping of the tubular portion 106.

Referring again to FIG. 5, the spherical portion 112 may define one or more mounting cavities 128 for receiving one or more auxiliary attachments 130 (FIGS. 8-10), which will be discussed in greater detail below. The one or more mounting cavities 128 extend axially inward from the spherical portion side surface 116. In the embodiment shown in FIG. 5, the spherical portion 112 defines one mounting cavity 128. Nevertheless, the spherical portion 112 may define zero, two, three, four, or more mounting cavities 128 in alternate embodiments. As shown in FIG. 5, the mounting cavity 128 is positioned radially outwardly from the passage 118.

In the embodiment shown in FIG. 3, the sleeve 102 and the end cap 104 are separate components. In alternate embodiments, however, the sleeve 102 and the end cap 104 may be a single component. For example, the sleeve 102 and the end cap 1004 may be integrally formed or fixedly coupled, e.g., via welding.

Figure 6:
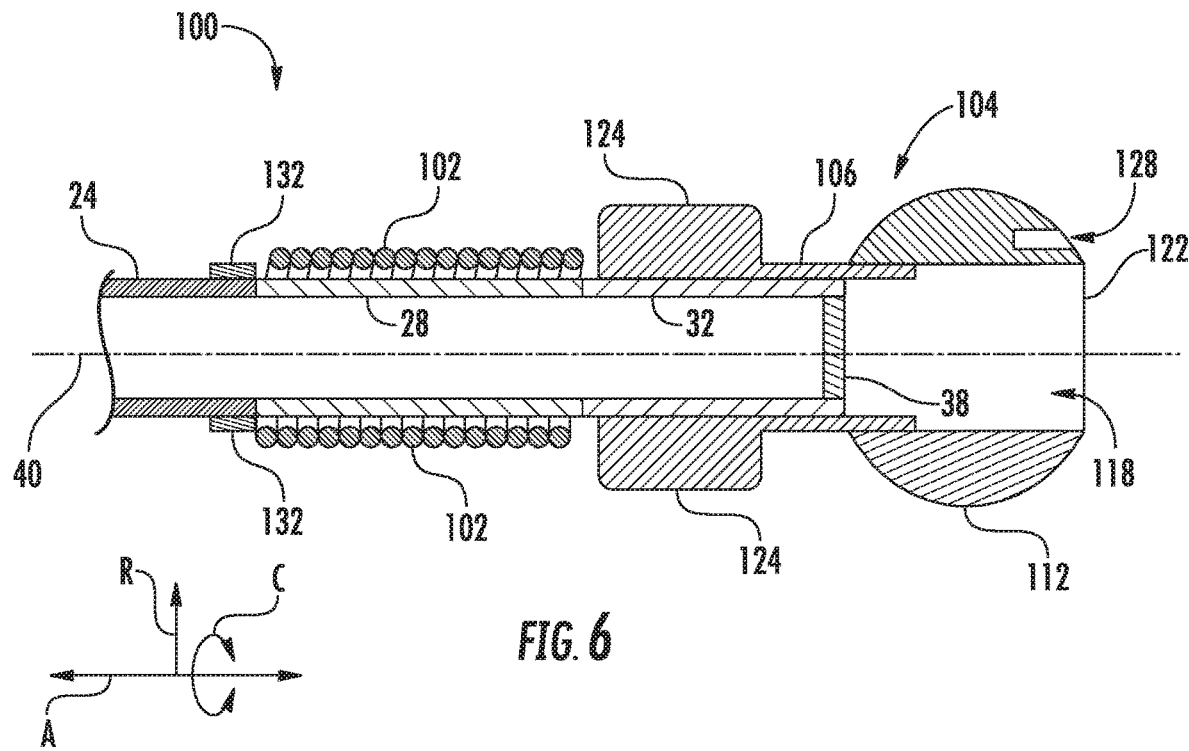
FIG. 6 is a cross-sectional view of the borescope wand protection system coupled to the borescope wand shown in FIG. 3 taken generally about line 6-6.
Figure 7:
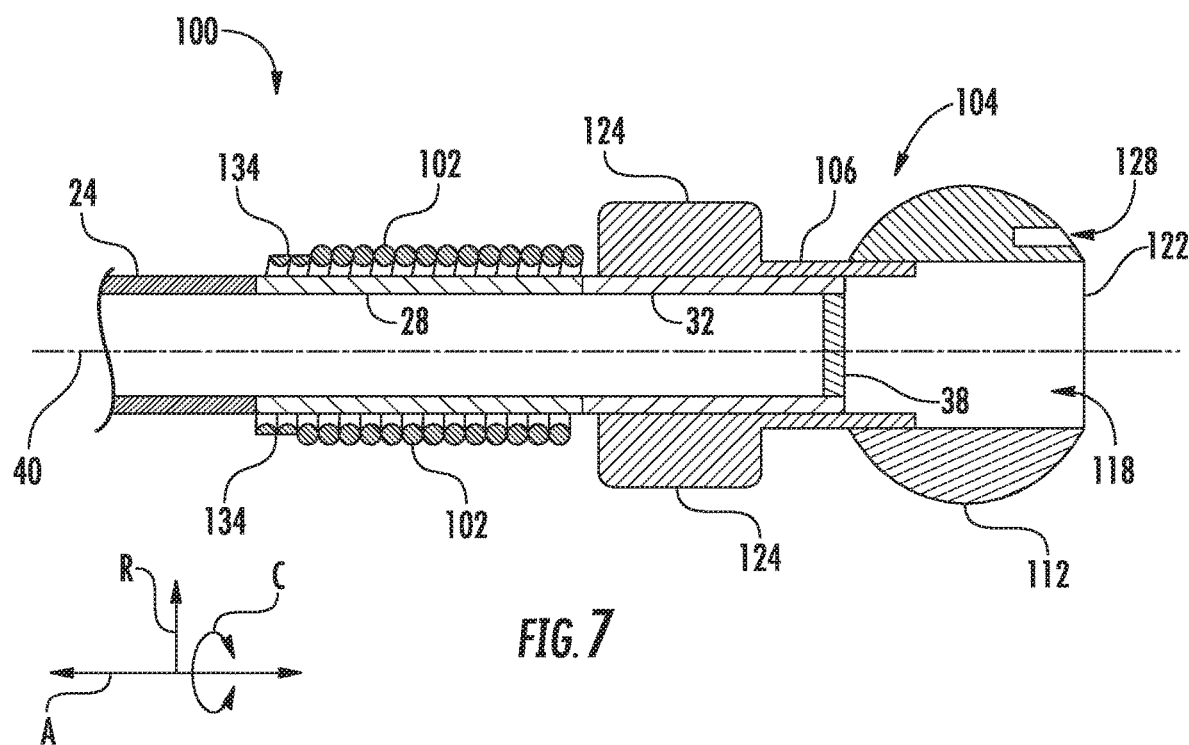
FIG. 7 is an alternate cross-sectional view of the borescope wand protection system coupled to the borescope wand, illustrating a crimped portion coupling the sleeve to the borescope wand according to embodiments of the present disclosure.

FIGS. 6 and 7 are cross-sectional views of embodiments of the borescope wand protection system 100 when coupled to the borescope wand 14. More specifically, the end cap 104 may be removably secured to the lens end 32 of the borescope wand 14. In some embodiments, for example, the spherical portion 112 of the end cap 104 may squeeze the tubular portion 106 of the end cap 104 against the lens end outer surface 34 of the borescope wand 14, thereby securing the end cap 104 to the lens end 32. More specifically, the lens end 32 may be positioned in the portion of the passage 118 defined by the tubular portion 106 of the end cap 104 as will be discussed in greater detail below. The spherical portion 112 of the end cap 104 then threadingly couples to the tubular portion 106, thereby squeezing the tubular portion 106 against the lens end outer surface 34. Once coupled, the end cap 104 is unable to slide off of the lens end 32 of the borescope wand 14, i.e., slide axially past the side surface 36 (FIG. 2). In other embodiments, end cap 104 may secure to the lens end 32 via a set screw (not shown), a grommet (not shown), or any other suitable method.

As shown in FIGS. 6 and 7, the lens end 32 is positioned in the passage 118 defined by the end cap 104 when the end cap 104 is removably coupled to the borescope wand 14. In particular, the lens end 32 extends through the first opening 120 and is positioned within the passage 118 such that the lens 38 is axially positioned between the first opening 120 and the second opening 122. In the embodiments shown in FIGS. 6 and 7, the lens end 32 is positioned entirely within the portion of the passage 118 defined by the tubular portion 106 of the end cap 104. In such embodiments, the lens 38 and the second opening 122 are axially spaced apart, which further protects the lens 38 from scratching or other damage. Nevertheless, the lens end 32 may positioned partially within the portion of the passage 118 defined by the spherical portion 112 of the end cap 104 in other embodiments.

As mentioned above and shown in FIGS. 3, 6, and 7, the sleeve 102 is positioned around the articulating portion 28 of the borescope wand 14 to protect the same. As depicted therein, the sleeve 102 is axially spaced apart from the lens 38 by at least a portion of the tubular portion 106 of the end cap 104. Furthermore, the end cap 104 prevents the sleeve 102 from sliding off of the articulating portion 28 of the borescope wand 14 and onto the lens end 32. That is, the end cap 104 circumscribes the maximum axial distance away from the body portion 12 (FIG. 1) of the borescope 10 that the sleeve 102 may travel.

In the embodiment shown in FIG. 6, a ring 132 may be positioned around and coupled to the base portion outer surface 26 of the borescope wand 14. The ring 132 may prevent the sleeve 102 from sliding off of the articulating portion 28 and onto the base portion 24 of the borescope wand 14. That is, the ring 132 circumscribes the maximum axial distance toward the body portion 12 (FIG. 1) of the borescope 10 that the sleeve 102 may travel. As shown, the sleeve 102 is axially positioned between the ring 132 and the lens end 32 of the borescope wand 14. In some embodiments, the ring 132 may be a plurality of layers of tape (e.g., a Teflon tape, etc.) wrapped around the base portion outer surface 26. Nevertheless, the ring 132 may be a solid integral component such as a metallic or plastic ring instead.

In the embodiment shown in FIG. 7, the sleeve 102 includes a crimped portion 134 that prevents the sleeve 102 from sliding off of the articulating portion 28. More specifically, a portion of the sleeve 102 proximate to the base portion 24 of the borescope wand 14 may be crimped, thereby forming the crimped portion 134. As such, the crimped portion 134 squeezes the articulating portion outer surface 30 to prevent axial movement of the sleeve 102 along the borescope wand 14. The crimped portion 134 may be in addition to or in lieu of the ring 134. In alternate embodiments, however, any suitable structure or method may be used to prevent the sleeve 102 from sliding off of the articulating portion 28. For example, the sleeve 102 may couple to the end cap 104, which, as discussed above, couples to the borescope wand 14.

FIGS. 8-10 illustrate various embodiments of the one or more auxiliary attachments 130. As used herein, the term "auxiliary attachment" refers to any tool that couples to the spherical portion 112 of the end cap 104 and extends outwardly therefrom. As mentioned above, the spherical portion 112 defines one or more mounting cavities 128 (FIGS. 6 and 7), which receive the one or more auxiliary attachments 130. In this respect, the one or more auxiliary attachments 130 are axially spaced apart from the lens 38. As will be discussed in greater detail below, the one or more auxiliary attachments 130 may be used for manipulating or retrieving nearby objects (e.g., debris), cleaning nearby surfaces or features, modifying nearby surfaces or features, or any other similar purpose.

In the embodiment shown in FIG. 8, the auxiliary attachment 130 is a hook 136, which may be used to manipulate or retrieve debris or other objects positioned near the end cap 104. More specifically, the hook 136 is received into one of the mounting cavities 128 and extends generally axially outwardly from the spherical portion side surface 116. The hook 136 may have any suitable shape and/or configuration.

FIG. 9 illustrates an embodiment where the auxiliary attachment 130 is an abrasive element 138 coupled to a shaft 140, which may be used to clean or modify (e.g., remove corrosion, burrs, etc.) nearby surfaces or features. In particular, the shaft 140 includes a first end 142 and a second end 144 axially spaced apart from the first end 142. The first end 142 of the shaft 140 is received into one of the mounting cavities 128. The abrasive element 138 couples to the second end 144 of the shaft 140. In this respect, the shaft 140 and the abrasive element 138 extend generally axially outwardly from the spherical portion side surface 116. As such, the spherical portion 112 of the end cap 104 and the abrasive element 138 are axially spaced apart by the shaft 140. In the embodiment shown in FIG. 9, the abrasive element 138 is spherical. The abrasive element 138 is conical, however, in the embodiment shown in FIG. 10. Alternatively, the abrasive element 138 may have any suitable shape and/or configuration in other embodiments Although the auxiliary attachment 130 is described above in the context of the hook 136 and the abrasive element 138, the auxiliary attachment 130 may have any suitable structure or function. For example, the auxiliary attachment 130 may be a brush (not shown) in some embodiments.

As discussed in greater detail above, the sleeve 102 protects the articulating portion 28 of the borescope wand 14 from damage caused by contact with, e.g., various gas turbine components. Similarly, the end cap 104 protects the lens end 32 of the borescope wand 14 from damage as well. In this respect, the borescope wand 14 experiences less wear than borescope wands not coupled to the borescope wand protection system 100, thereby increasing the service life of the borescope 10. This reduced wear also decreases the number of maintenance intervals necessary during the service life of the borescope 10. Furthermore, the end cap 104 protects the lens 38 from scratching or other damage.

The borescope wand protection system 100 is described above in the context protecting the borescope wand 14 from damage caused by contact with various gas turbine components. Nevertheless, the borescope wand protection system 100 may be used to protect the borescope wand 14 from damage caused during the inspection of any suitable component or feature (e.g., steam turbines, diesel engines, machinery, guns, building walls, etc.).

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A borescope, comprising:
   a borescope wand comprising a base portion, an articulating portion, and a lens end;
   a single outermost surface of the borescope wand extending continuously from the base portion to the lens end, the single outermost surface of the borescope wand including a base portion outermost surface extending to the articulating portion and an articulating portion outermost surface extending from the base portion to the lens end;
   a lens positioned in the lens end of the borescope wand;
   a sleeve positioned externally around the articulating portion outermost surface of the borescope wand, the sleeve being spaced apart from the lens; and
   an end cap defining a passage extending therethrough from a first opening to a second opening, the end cap comprising a spherical portion that defines a mounting cavity positioned radially outwardly from the passage, wherein the lens end of the borescope wand extends through the first opening and is positioned within the passage such that the lens is positioned between the first opening and the second opening.

2. The borescope of claim 1, wherein the sleeve is metallic.

3. The borescope of claim 1, wherein the sleeve is a helical spring.

4. The borescope of claim 1, further comprising:
   a ring coupled to the outermost surface of the borescope wand at a boundary of the base portion outermost surface and the articulating portion outermost surface, wherein the sleeve is positioned between the ring and the lens end of the borescope wand and axially constrained by the ring to prevent the sleeve from sliding off of the articulating portion and onto the base portion.

5. The borescope of claim 1, wherein the sleeve comprises a crimped portion coupling the sleeve to the outermost surface of the borescope wand, wherein the sleeve is axially constrained around the articulating portion outermost surface by the crimped portion.

6. The borescope of claim 1, further comprising:
   an auxiliary attachment extending outwardly from the end cap.

7. The borescope of claim 6, wherein the auxiliary attachment is a hook.

8. The borescope of claim 6, wherein the auxiliary attachment comprises:
   a shaft comprising a first end coupled to the end cap and a second end; and
   an abrasive element coupled to the second end of the shaft.

9. The borescope of claim 8, wherein the abrasive element is spherical or conical.

10. The borescope of claim 1, wherein the end cap further comprises a tubular portion, and wherein the tubular portion defines the first opening and the spherical portion defines the second opening.

11. The borescope of claim 10, wherein the spherical portion and the tubular portion are integrally coupled.

12. The borescope of claim 10, wherein the lens end of the borescope wand is positioned in the tubular portion of the end cap.

13. The borescope of claim 1, further comprising:
   an auxiliary attachment received by the mounting cavity, wherein the auxiliary attachment extends outwardly from the spherical portion of the end cap.

14. A borescope, comprising:
   a borescope wand extending along a longitudinal axis and comprising, in axial sequence, a base portion comprising a base portion outer surface, an articulating portion comprising an articulating portion outer surface, and a lens end comprising a lens end outer surface, the base portion outer surface, the articulating portion outer surface, and the lens end outer surface collectively defining a single continuous outer surface of the borescope wand;
   a lens positioned in the lens end of the borescope wand;
   a helical spring positioned around the articulating portion outer surface of the borescope wand, the helical spring being spaced apart from the lens; and
   an end cap comprising a tubular portion and a spherical portion integrally coupled to the tubular portion, the end cap defining an axial passage extending therethrough from a first opening defined in the tubular portion to a second opening defined in the spherical portion, wherein the spherical portion defines a mounting cavity positioned radially outwardly from the axial passage, and wherein the lens end of the borescope wand extends through the first opening into the tubular portion of the end cap and is positioned within the axial passage such that the lens is positioned between the first opening and the second opening.

15. The borescope of claim 14, further comprising:
an auxiliary attachment extending outwardly from the end cap, wherein the auxiliary attachment is spaced apart from the lens.

16. The borescope of claim 15, wherein the auxiliary attachment is a hook.

17. The borescope of claim 15, wherein the auxiliary attachment comprises:
a shaft comprising a first end coupled to the end cap and a second end; and
an abrasive element coupled to the second end of the shaft.

18. The borescope of claim 1, wherein the borescope wand extends along a longitudinal axis, and wherein the sleeve extends axially from a boundary of the base portion outermost surface and the articulating portion outermost surface and is axially spaced apart from the lens.

\* \* \* \* \*